US011464455B2

(12) United States Patent
Villazón-Terrazas et al.

(10) Patent No.: US 11,464,455 B2
(45) Date of Patent: Oct. 11, 2022

(54) METHOD AND APPARATUS OF CONTEXT-BASED PATIENT SIMILARITY

(71) Applicant: Fujitsu Limited, Kawasaki (JP)

(72) Inventors: Boris Villazón-Terrazas, Madrid (ES); Bo Hu, Winchester (GB); Victor De La Torre, Madrid (ES)

(73) Assignee: FUJITSU LIMITED, Kawasaki (JP)

( * ) Notice: Subject to any disclaimer, the term of this patent is extended or adjusted under 35 U.S.C. 154(b) by 599 days.

(21) Appl. No.: 15/718,759

(22) Filed: Sep. 28, 2017

(65) Prior Publication Data

US 2018/0098737 A1    Apr. 12, 2018

(30) Foreign Application Priority Data

Oct. 6, 2016   (DE) .................... 102016219432.1

(51) Int. Cl.
*G16H 50/70*   (2018.01)
*G16H 50/20*   (2018.01)
(Continued)

(52) U.S. Cl.
CPC .......... *A61B 5/7275* (2013.01); *A61B 5/0022* (2013.01); *G06N 5/022* (2013.01);
(Continued)

(58) Field of Classification Search
CPC ....... A61B 5/7275; G06F 19/30; G06F 19/32; G06F 19/34; G06F 19/3456;
(Continued)

(56) References Cited

U.S. PATENT DOCUMENTS 10,431,339 B1 * 10/2019 Cornelius .............. G16H 10/60
2001/0054033 A1   12/2001 Sato et al.
(Continued)

FOREIGN PATENT DOCUMENTS

JP    2012-043113 A    3/2012

OTHER PUBLICATIONS

Extended European Search Report dated Feb. 5, 2018 in corresponding European Patent Application No. 17166976.5, 11 pages.
(Continued)

*Primary Examiner* — John P Go
*Assistant Examiner* — Christopher B Wehrly
(74) *Attorney, Agent, or Firm* — Staas & Halsey LLP

(57) ABSTRACT

A computer apparatus to assist diagnosis of a patient including: a memory storing instructions for execution and an output for results of a processor that provides a patient builder and a vertex filter. Where the builder inputs patient data including historical clinical; and open data, and to create a patient clinical object, PCO, graph; and a full patient graph PCOs for each patient. The filter includes: a context builder to build a domain based on a specification and open data; a context-based vertex filter ranking vertices in the full patient graph based on domain affiliation, retaining any vertices with high domain affiliation; and computing a similarity between the patient PCO and other PCOs in the full patient graph using the retained vertices; and a patient ranker ranks the PCOs according to t similarity where the output lists patients similar to the patient to suggest patient diagnoses.

13 Claims, 7 Drawing Sheets

(51) Int. Cl.
  *A61B 5/00* (2006.01)
  *G06N 20/00* (2019.01)
  *G16H 10/60* (2018.01)
  *G16H 20/10* (2018.01)
  *G16H 20/90* (2018.01)
  *G16H 50/50* (2018.01)
  *G16H 20/70* (2018.01)
  *G06N 5/02* (2006.01)
  *G06N 5/04* (2006.01)
  *G06Q 10/10* (2012.01)

(52) U.S. Cl.
  CPC .............. *G06N 5/04* (2013.01); *G06N 20/00* (2019.01); *G06Q 10/10* (2013.01); *G16H 10/60* (2018.01); *G16H 20/10* (2018.01); *G16H 20/70* (2018.01); *G16H 20/90* (2018.01); *G16H 50/20* (2018.01); *G16H 50/50* (2018.01); *G16H 50/70* (2018.01)

(58) Field of Classification Search
  CPC ............. G06F 19/3462; G06F 19/3468; G06F 19/3475; G06F 19/3481; G06Q 50/22; G06Q 50/24; G16H 10/60; G16H 20/10; G16H 20/70; G16H 20/90; G06N 5/022; G06N 5/04
  USPC .......................................................... 705/3
  See application file for complete search history.

(56) References Cited

U.S. PATENT DOCUMENTS

| | | | |
|---|---|---|---|
| 2003/0130973 A1* | 7/2003 | Sumner, II | G06F 19/3481 706/45 |
| 2006/0161556 A1* | 7/2006 | Dettinger | G06F 16/20 |
| 2008/0201280 A1* | 8/2008 | Martin | G16H 50/20 706/12 |
| 2012/0041772 A1 | 2/2012 | Ebadollahi et al. | |
| 2012/0136882 A1 | 5/2012 | Kawagishi et al. | |
| 2012/0265550 A1* | 10/2012 | Friedlander | G06Q 10/06 705/2 |
| 2013/0226616 A1* | 8/2013 | Nigam | G06Q 10/00 705/3 |
| 2013/0231953 A1 | 9/2013 | Ebadollahi et al. | |
| 2013/0297342 A1 | 11/2013 | Duplay | |
| 2014/0288387 A1 | 9/2014 | Duplay | |
| 2016/0063212 A1* | 3/2016 | Monier | G16H 50/50 705/3 |

OTHER PUBLICATIONS

Notice of Reasons for Refusal dated Mar. 23, 2021 in related Japanese Patent Application No. 2017-169974 (5 pages) (5 pages English Translation).

German Search Report dated Jun. 22, 2017 in German Patent Application No. 10 2016 219 432.1.

Keyvanpour, Mohammad Reza, et al. "Classification and Analysis of Frequent Subgraphs Mining Algorithms" Journal of Software, 2012, 7. Jg., Nr. 1,S. 220-227*.

Longhurst, Christopher A et ai.. "A 'green button' for using aggregate patient data at the point of care". Health Affairs, 2014, 33. Jg., Nr. 7, S. 1229-1235*.

Ping Zhang, et al. "Towards Personalized Medicine: Leveraging Patient Similarity and Drug Similarity Analytics" http://www.ncbi.nlm.nih.gov/pmc/articles/PMC4333693/, 5 pages.

Sebastian Klenk et al., "Determining Patient Similarity in Medical Social Networks", MEDEX 2010 Proceedings, http://ceur-ws.org/VOl-572/paper1.pdf, 8 pages.

Jimeng Sun, et al., "Supervised Patient Similarity Measure of Heterogeneous Patient Record", SIGKDD Explorations, vol. 14. Issue 1, 9 pages http://www.kdd.org/exploration_files/V14-01-03-Sun.pdf.

"Center for Computational Health", IBM Research, 2017, 15 pages http://www.research.ibm.com/healthcare/projects_patientsimiiarity.shtml.

* cited by examiner

METHOD AND APPARATUS OF CONTEXT-BASED PATIENT SIMILARITY

CROSS-REFERENCE TO RELATED APPLICATIONS

This application claims the benefit of German Application No. 102016219432.1, filed Oct. 6, 2016, in the German Intellectual Property Office, the disclosure of which is incorporated herein by reference.

BACKGROUND

The embodiments relate to diagnosis, prognosis and treatment of an individual or a living subject, usually referred to as a patient. The patient may be a human or potentially an animal, such as a specimen of a rare breed or even a pet. In many scenarios, the patient may already be suffering from a disorder, but in others the patient is currently healthy, and thus the term medical condition includes conditions such as pregnancy, as well as disorders, illnesses and diseases. The embodiments are thus widely applicable in medicine, healthcare and veterinary science.

Providing an accurate diagnosis for a patient is a challenging task. Years of study and daily practice provide clinicians (for example these could include nurses, doctors, dentists, healthcare practitioners and veterinary practitioners) with the skills necessary to estimate this diagnosis. The accuracy of this estimation is crucial to provide the patient with the right treatment. However due to the complexity of the task, a high level of accuracy is not always achieved. An error at the diagnosis level has a deep impact on patient health, since almost all treatments have secondary effects. In the case of mental health, for example, estimating the right diagnosis could be even a more difficult task given the complexity of human behavior.

Nowadays, diagnostic errors (which can be defined as a diagnosis that is missed, wrong or delayed, as detected by some subsequent definitive test or finding) are clinically and financially more costly than even before. Moreover, diagnostic errors are the leading cause of medical malpractice claims in the U.S. and are estimated to cause 40000-80000 deaths annually.

There are several factors that affect the accuracy of the diagnosis estimation:
- Clinicians have a very short time to see the patient;
- Diagnoses are not obvious in many cases, since several symptoms might be simultaneously present;
- The "resolution" of the diagnosis has to meet the existent treatments;
- A given patient is diagnosed by different class of clinicians, from several specialties and different levels of knowledge;
- Previous diagnoses recorded in the databases might not reflect the real condition of the patient due to errors when such previous diagnoses are recorded in the information system.

Consequently, assisting clinicians during the diagnosis process will reduce the diagnosis errors and therefore will improve the efficiency of the healthcare system and also reduce costs by avoiding undesirable secondary effects. The same also applies to prescribed treatments. It is also desirable to assist the estimation of prognosis.

Personalized medicine is an area that could be of assistance, not just in diagnosis but in subsequent processes such as prognosis, treatment risk stratification and clinical pathway analysis. It aims to tailor treatment to the individual characteristics of each patient. This requires the ability to classify patients into subgroups with predictable response to a specific treatment. Although there are already many examples of personalized medicine by leveraging genetics/genomics information in current practice, such information is not yet widely available in every day clinical practice.

With the tremendous growth of the adoption of electronic health records (EHR), various sources of clinical information, e.g., demographics, diagnostic history, medications, laboratory test results, vital signs, among others, are becoming available about patients. Recently some treatment comparison studies were conducted based on data from EHR of a cohort of clinically similar patients who received the treatments previously and whose outcomes were recorded. There are also some studies of combining clinical and genetics/genomics information in selecting optimal clinical treatments.

SUMMARY

According to an embodiment of a first aspect, there is provided a computer apparatus to assist diagnosis of a medical condition in a patient to be diagnosed, comprising: a memory storing instructions for execution by a processor and an output for outputting results of the processor, the processor configured by the instructions to provide a patient builder and a vertex filter; wherein the patient builder is arranged to input patient data including historical clinical data for a population of patients; and to input open data, and to use these inputs to create a patient clinical object (PCO), which represents each patient in the form of a graph; and a full patient graph composed of a PCO for each patient; the vertex filter includes: a patient context builder to input specification of a medical domain and open data and to build a domain corpus based on the specification of the medical domain and on the open data; a context-based vertex filter to rank vertices in the full patient graph based on their domain affiliation with respect to the domain corpus and to retain any vertices with high domain affiliation in each PCO, and to compute a similarity between the PCO of the patient to be diagnosed and other PCOs in the full patient graph on the basis of the retained vertices; and a patient ranker to rank the PCOs according to the computed similarity; and wherein the output is arranged to output a list of patients similar to the patient to be diagnosed, to suggest one or more diagnoses of the patient.

Comparison of the patient to be diagnosed with the similar patients may even provide a predicted primary diagnosis or treatment or prognosis, based on the population of patients. The population of patients should be large enough to include a range of different patients. For example it could be taken from a single hospital or from a regional population from a geographical region in a country, or from a wider population, for example for a country. The processor may provide results to the output by retaining and transferring to the output PCOs about threshold relevance, and the list which is output can have any suitable form, such as PCOs presented in order of relevance. The output of the predicted primary diagnosis may be displayed to a clinician on screen, or provided in any other suitable way, for example as a print out or email.

The method of the embodiments combines the use of specific data on a population of patients with open data in a way that allows the relevant data in the population to be specified and highlighted, to provide an output which can materially assist a clinician.

The computer apparatus may further comprise an episode grouper within the patient context builder which groups vertices of a PCO into time-based episodes. This may separate unrelated parts of the same PCO (for example for different conditions), which might otherwise be automatically linked and thus detrimentally affect the accuracy of the method.

The episode grouper may group the vertices using a time stamp of data creation, or any other suitable methodology, for example by taking into account an underlying condition and whether the symptoms, for example, match the condition and the normal course of the condition.

If there is an episode grouper, the context-based vertex filter and the patient ranker may process each episode of a PCO separately (and each PCO separately).

The PCO may be a graph centred on a patient ID vertex, with edges linking the patient ID vertex to labelled vertices representing historical clinical data, wherein the vertices representing historical clinical data each belong to a category. The edges may be labelled with the category, which may be a category of medical information, such as any of diagnosis, symptom, medication, treatment, disease, for example.

The context-based vertex filter in the vertex filter may be to group vertices in a PCO of the same category together and to calculate the similarity of the grouped vertices with vertices of the same category in the PCO of the patient to be diagnosed, using the vertex labels (or vertex attributes).

The context-based vertex filter may also adjust the calculated similarity of the grouped vertices with vertices of the same category in the PCO of the patient to be diagnosed, by applying an affinity value referring to the affinity (of the vertex label) with the domain corpus.

Further the patient ranker may calculate an aggregate similarity of a PCO with the PCO of the patient to be diagnosed, based on the similarities of the grouped vertices in the PCO to the vertices of the same category in the PCO of the patient to be diagnosed. This similarity is only of the retained vertices, so only the vertices that are relevant to the medical domain which has been specified. Hence patient ranking comes after the similarity computation. Ranking may also implicitly involve user interaction. For example, the system may present the list of similar patients in a front-end UI and the user may modify the list, for example to either confirm or reject an existing ranking order or adjust the order of this list, or delete one or more entries etc. In the end a contextualized list of similar patients is the output.

Much clinical data is textual, but the historical clinical data may include non-textual data and the patient builder may then include an extractor to extract textual descriptions from the non-textual data. In this case, each extracted textual description may become a labeled vertex of a PCO, the labeled vertex being linked to an address where the non-textual data is stored.

The computer apparatus may be able to update data in a PCO dynamically, and to this end the patient builder may accept input from an automated data crawler, to update the PCO incrementally.

The patient context builder in the vertex filter may provide the domain corpus in the form of a domain-specific list of vectors, each embedding a term defining the domain, with the values of the vector indicating the significance of the term.

The patient builder may additionally act to accept expert knowledge in the form of clinician's rules, to verify any diagnoses in the PCO.

The input for open data may allow input of data from more than one source, for example from specialist medical databases, as well as non-specialist sources such as Wikipedia.

The context-based vertex filter may retain any vertices with high domain affiliation in each PCO by filtering out vertices with a domain affiliation below a threshold, or by ranking the vertices in order of domain affiliation and selecting a predefined number of vertices starting from the highest domain affiliation.

According to an embodiment of a second aspect, there is provided a computer-implemented method of assisting diagnosis of a medical condition in a patient to be diagnosed, comprising: inputting patient data including historical clinical data for a population of patients; and inputting open data, and using these inputs to create a patient clinical object, PCO representing each patient in the form of a graph; and a full patient graph composed of a PCO for each patient; receiving a specification of a medical domain; and open data and building a domain corpus based on the specification of the medical domain and on the open data; ranking vertices in the full patient graph based on their domain affiliation with respect to the domain corpus and retaining any vertices with high domain affiliation in each PCO; computing a similarity between the PCO of the patient to be diagnosed and other PCOs in the full patient graph on the basis of the retained vertices to rank the PCOs; and outputting a (ranked) list of patients similar to the patient to be diagnosed. This can effectively assist a clinician in diagnosis by suggesting one or more diagnoses of one or more of the most similar (top ranked) patients.

According to an embodiment of a third aspect, there is provided a computer program which when executed on a computer carries out a method of assisting diagnosis of a medical condition in a patient to be diagnosed, comprising: inputting patient data including historical clinical data for a population of patients; and inputting open data, and using these inputs to create a patient clinical object (PCO) representing each patient in the form of a graph; and a full patient graph composed of a PCO for each patient; receiving a specification of a medical domain; and open data and building a domain corpus based on the specification of the medical domain and on the open data; ranking vertices in the full patient graph based on their domain affiliation with respect to the domain corpus and retaining any vertices with high domain affiliation in each PCO; computing a similarity between the PCO of the patient to be diagnosed and other PCOs in the full patient graph on the basis of the retained vertices to rank the PCOs; and outputting a (ranked) list of patients similar to the patient to be diagnosed, to suggest one or more diagnoses of the patient.

The method or computer program according to preferred embodiments may comprise any combination of the apparatus aspects. Methods or computer programs according to further embodiments may be described as computer-implemented in that they require processing and memory capability.

The apparatus according to preferred embodiments is described as configured or arranged to, or simply "to" carry out certain functions. This configuration or arrangement could be by use of hardware or middleware or any other suitable system. In preferred embodiments, the configuration or arrangement is by software.

Thus according to one aspect there is provided a program which, when loaded onto at least one computer configures the computer to become the apparatus according to any of the preceding apparatus definitions or any combination thereof.

According to a further aspect there is provided a program which when loaded onto the at least one computer configures the at least one computer to carry out the method steps according to any of the preceding method definitions or any combination thereof.

In general the computer may comprise the elements listed as being configured or arranged to provide the functions defined. For example this computer may include memory, processing, and a network interface which can provide both input and output functionality.

The invention can be implemented in digital electronic circuitry, or in computer hardware, firmware, software, or in combinations of them. The embodiments can be implemented as a computer program or computer program product, i.e., a computer program tangibly embodied in a non-transitory information carrier, e.g., in a machine-readable storage device, or in a propagated signal, for execution by, or to control the operation of, one or more hardware modules.

A computer program can be in the form of a stand-alone program, a computer program portion or more than one computer program and can be written in any form of programming language, including compiled or interpreted languages, and it can be deployed in any form, including as a stand-alone program or as a module, component, subroutine, or other unit suitable for use in a data processing environment. A computer program can be deployed to be executed on one module or on multiple modules at one site or distributed across multiple sites and interconnected by a communication network.

Method steps of the embodiments can be performed by one or more programmable processors executing a computer program to perform functions of the embodiments by operating on input data and generating output. Apparatus of the embodiments can be implemented as programmed hardware or as special purpose logic circuitry, including e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for executing instructions coupled to one or more memory devices for storing instructions and data.

The embodiments are described in terms of particular embodiments. Other embodiments are within the scope of the following claims. For example, the steps of the embodiments can be performed in a different order and still achieve desirable results. Multiple test script versions can be edited and invoked as a unit without using object-oriented programming technology; for example, the elements of a script object can be organized in a structured database or a file system, and the operations described as being performed by the script object can be performed by a test control program.

Elements of the embodiments have been described using the terms "vertex filter", "patient builder", and "patient context builder" etc. The skilled person will appreciate that such functional terms and their equivalents may refer to parts of the system that are spatially separate but combine to serve the function defined. Equally, the same physical parts of the system may provide two or more of the functions defined. For example, separately defined means may be implemented using the same memory and/or processor as appropriate.

BRIEF DESCRIPTION OF THE DRAWINGS

Preferred features of the embodiments will now be described, purely by way of example, with references to the accompanying drawings, in which.

DETAILED DESCRIPTION

Figure 1:
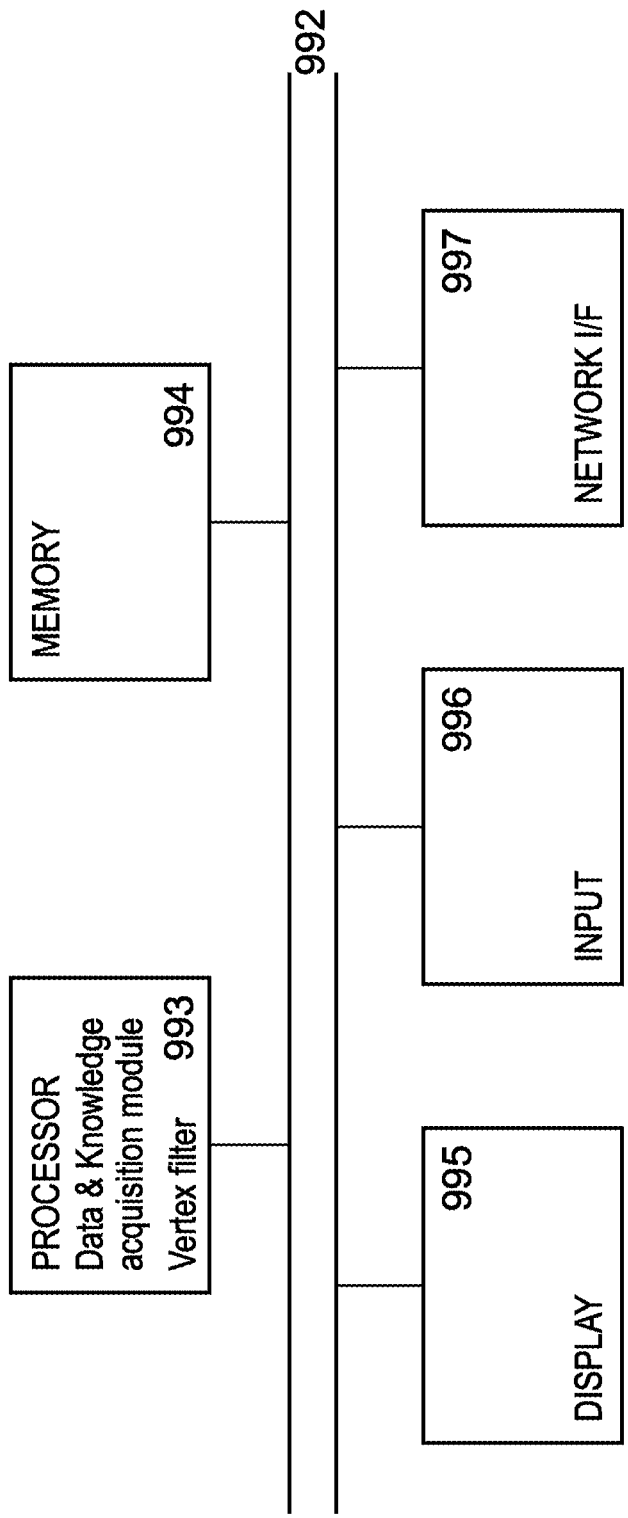
FIG. 1 is a block diagram of main system components in a general embodiment.

Reference will now be made in detail to the embodiments, examples of which are illustrated in the accompanying drawings, wherein like reference numerals refer to the like elements throughout. The embodiments are described below to explain the embodiments by referring to the figures.

In the related art known to the inventors:

Patient similarity is frequently approached based on selected attributes of patients. Typically such attributes include patient demographic features, symptoms and signs, personal medical history, family medical history, behaviors, diet, etc.

The list of contributing features/attributes can be very long so as to provide a comprehensive view of patients.

In practice, exhaustive comparison of all patient attributes is either very expensive to perform as part of online analysis or divertive wherein potentially irrelevant attributes can mask core ones that present the most diagnostic values.

The inventors have come to the conclusion that it is important to provide an adaptive and context aware similarity measure giving more emphasis on the most critical patient attributes, aligned with a patient's situation and with the domain of discourse.

The inventors believe that tasks of clinicians are largely based on training and experience. It is common that one clinician shares the diagnostic passage with others and draws knowledge and conclusions from the experiences from others. At the heart of medical diagnostic knowledge sharing lays the fast and accurate identification of historical cases that are similar to the case to be considered. Computing patient similarity, however, is not straightforward and can involve a whole raft of influencing factors.

Existing approaches using clinical information for personalized medicine rely on large amounts of real-world data regarding the target treatment itself, which may not be available for new drugs or rarely-used treatments. Patient similarity analytics aims to find patients who display similar clinical characteristics to the patient of interest. With the right patient similarity in place, patient similarity analytics can be used in the target patient retrieval, medical prognosis, risk stratification, and clinical pathway analysis tasks.

Therefore, embodiments of the invention aim to offer
1. A method to collect patient data from different sources
2. A mechanism to store patient data for analysis
3. An adaptive similarity measure to compare and contrast patients
4. A system that takes one patient case, searches the entire patient database to find similar ones and ranks the outcomes based on certain criteria In modern medicine, clinicians often draw their diagnostic conclusions from multiple sources of knowledge including past and established cases. Such cases are recalled to compare and contrast with the target patient case. Diagnoses, prognoses, and treatments are then derived using such established cases as references. In order to find the correct historical cases, the inventors have designed an accurate similarity measure that, given the data of two patients, can compute a numeric value to signify how similar the two patients are. This numeric value can also be treated as the confidence level indicating the extent to which a similarity computation considers that the two patients should be handled in the same way with respect to diagnosis, prognosis and treatment, for example.

The system of embodiments may be used as a standalone patient data management system or as an extension or a plug-in for an existing hospital information system.

FIG. 1 is a block diagram of a computing device, such as a data storage server and which may be used to implement a method of an embodiment of assisting diagnosis. The computing device comprises a processor 993, and memory, 994. The processor 993 is shown as including the two principal modules of the embodiments, a data and knowledge acquisition module and a vertex filter. The computing device also includes a network interface 997 for output and input over a network, which is for communication with other computing devices, for example with other computing devices of the embodiments.

For example, an embodiment may be composed of a network of such computing devices. The computing device also includes one or more manual input mechanisms such as keyboard and mouse 996, and another output as a display unit such as one or more monitors 995. The components are connectable to one another via a bus 992.

The memory 994 may include a computer readable medium, which term may refer to a single medium or multiple media (e.g., a centralized or distributed database and/or associated caches and servers) configured to carry computer-executable instructions or have data structures stored thereon. Computer-executable instructions may include, for example, instructions and data accessible by and causing a general purpose computer, special purpose computer, or special purpose processing device (e.g., one or more processors) to perform one or more functions or operations. Thus, the term "computer-readable storage medium" may also include any medium that is capable of storing, encoding or carrying a set of instructions for execution by the machine and that cause the machine to perform any one or more of the methods of the present disclosure. The term "computer-readable storage medium" may accordingly be taken to include, but not be limited to, solid-state memories, optical media and magnetic media. By way of example, and not limitation, such computer-readable media may include non-transitory computer-readable storage media, including Random Access Memory (RAM), Read-Only Memory (ROM), Electrically Erasable Programmable Read-Only Memory (EEPROM), Compact Disc Read-Only Memory (CD-ROM) or other optical disk storage, magnetic disk storage or other magnetic storage devices, flash memory devices (e.g., solid state memory devices).

The processor 993 is configured to control the computing device and execute processing operations, for example executing code stored in the memory to implement the various different functions of the data and knowledge acquisition module, the patient builder, the vertex filter, the patient context builder, the context-based vertex filter and the patient ranker described here and in the claims. The memory 994 stores data being read and written by the processor 993. As referred to herein, a processor may include one or more general-purpose processing devices such as a microprocessor, central processing unit, or the like. The processor may include a complex instruction set computing (CISC) microprocessor, reduced instruction set computing (RISC) microprocessor, very long instruction word (VLIW) microprocessor, or a processor implementing other instruction sets or processors implementing a combination of instruction sets. The processor may also include one or more special-purpose processing devices such as an application specific integrated circuit (ASIC), a field programmable gate array (FPGA), a digital signal processor (DSP), network processor, or the like. In one or more embodiments, a processor is configured to execute instructions for performing the operations and steps discussed herein.

The display unit 995 may display a representation of data stored by the computing device such as an individual PCO or a full patient graph and may also display a cursor and dialog boxes and screens enabling interaction between a user and the programs and data stored on the computing device. The input mechanisms 996 may enable a user to input data and instructions (for example a manual specification of a domain, or an indication of a patient to be diagnosed) to the computing device.

The network interface (network I/F) 997 may be connected to a network, such as the Internet, and is connectable to other such computing devices via the network. The network I/F 997 may control data input/output from/to other apparatus via the network. Other peripheral devices such as microphone, speakers, printer, power supply unit, fan, case, scanner, trackerball etc. may be included in the computing device.

The patient builder may comprise processing instructions stored on a portion of the memory 994, the processor 993 to execute the processing instructions, and a portion of the memory 994 to store the historical clinical data and other data during the execution of the processing instructions. The resultant PCO and agglomeration of PCOs as the full patient graph may be stored on the memory 994 and/or on a connected storage unit. Input to the knowledge and data processing module can use manual input as well as the network interface. For example manual input may be used to correct a PCO which has not formed properly for some reason.

The vertex filter may comprise processing instructions stored on a portion of the memory 994, the processor 993 to execute the processing instructions, and a portion of the memory 994 to store the interim products during the execution of the processing instructions. The resultant list of patients or specific diagnostic suggestions may be stored on the memory 994 and/or on a connected storage unit.

Looking at the individual components of the vertex filter, the patient context builder may comprise processing instructions stored on a portion of the memory 994, the processor 993 to execute the processing instructions, and a portion of the memory 994 to store the unfinished domain corpus in the form of individually computed vectors during the execution of the processing instructions. The finished domain corpus with all the relevant vectors may be stored on the memory 994 and/or on a connected storage unit. Input of the specification of the medical domain is likely to be by the user, but input of the open data is likely to be over the network interface.

The context-based vertex filter may comprise processing instructions stored on a portion of the memory 994, the processor 993 to execute the processing instructions, and a portion of the memory 994 to store the domain affiliation of vertices during the execution of the processing instructions. The set of retained vertices (in the form of parts of PCOs) may be stored on the memory 994 and/or on a connected storage unit.

The patient ranker may comprise processing instructions stored on a portion of the memory 994, the processor 993 to execute the processing instructions, and a portion of the memory 994 to store similarity of vertices during the execution of the processing instructions. The list of similar patients for output may be stored on the memory 994 and/or on a connected storage unit.

Methods of the embodiments may be carried out on a computing device such as that illustrated in FIG. 1. Such a computing device need not have every component illustrated in FIG. 1, and may be composed of a subset of those components. A method embodiment may be carried out by a single computing device in communication with one or more data storage servers via a network. The computing device may be a data storage itself storing the PCOs and the list of similar patients.

A method embodiment may be carried out by a plurality of computing devices operating in cooperation with one another. One or more of the plurality of computing devices may be a data storage server storing at least a portion of the PCOs and the list of similar patients.

Figure 2:
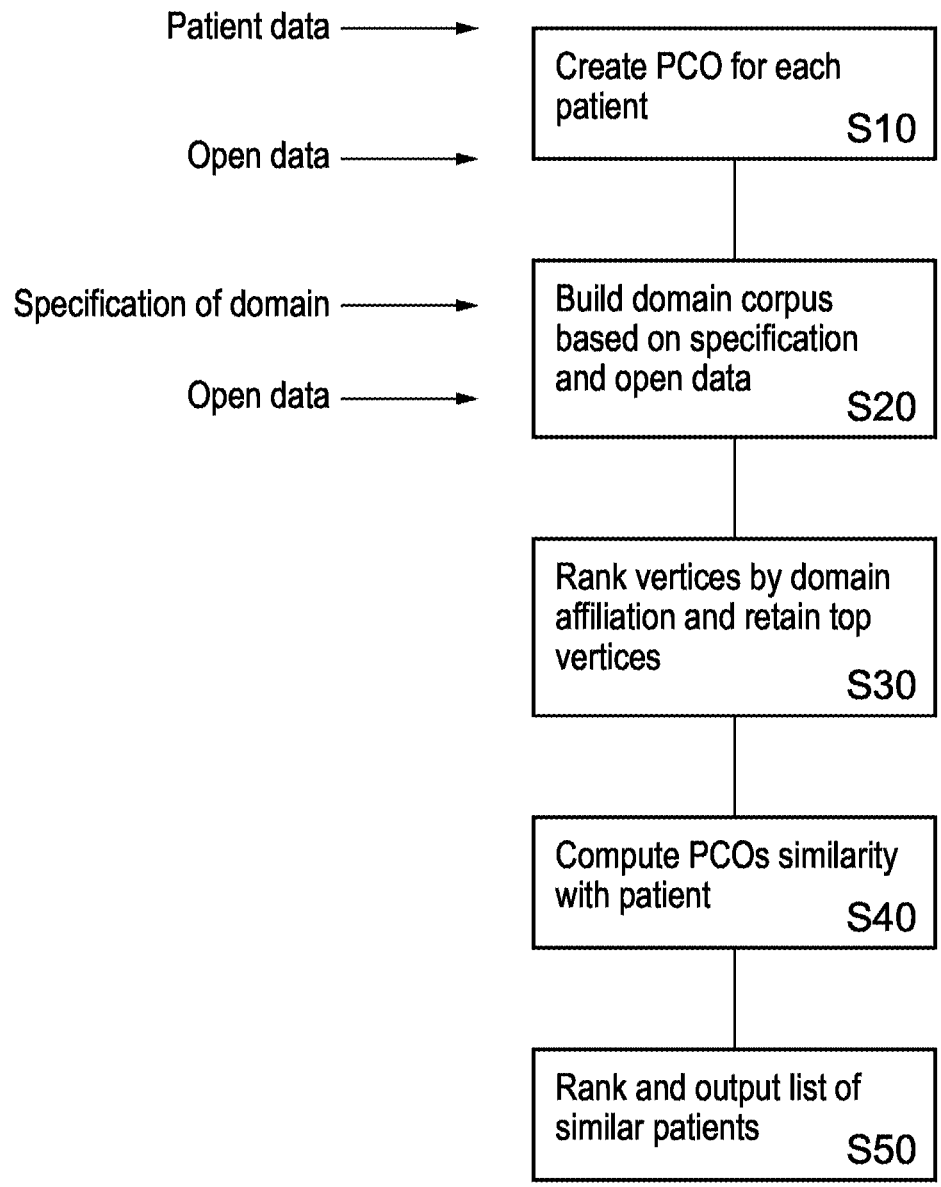
FIG. 2 is a flow chart of a method in a general embodiment.

FIG. 2 is a flowchart of a general method embodiment. In step S10, the method uses open data and patient data, including historical clinical data to create a PCO for each patient. Together, the PCOs are termed a full patient graph. There may be overlap between the PCOs (for example the same diagnosis) or they may be entirely separate.

In step S20, the domain corpus is created from input of a domain specification and input of open data.

In step S30, the domain corpus is used to rank the vertices (not including those that merely hold patient ID information, but including medical category vertices). Only the vertices which are linked to the domain are retained.

In step S40, the retained vertices are compared against the patient to be diagnosed, and this is then used to rank the PCOs. The identity of the patient to be diagnosed may be manually input before step S40, or at another time, such as before step S20 or S30.

In step S50 there is ranking and output of a list of similar patients, probably in ranked order. The output may be on a display, for example. It may be in text form or in graph form. The list of patients is likely to be of "top" patients with the highest similarity scores, by thresholding or by a pre-defined number, as before.

By means of the embodiments, a dynamic and adaptive context-based similarity measure is used. The resultant measurement varies based on the context wherein patient data are considered. This is essentially in line with how human experts comprehend data and how human experts evaluate whether an existing case can be referenced in decision making process, but includes a more specific filtering mechanism than human recollection.

Some key features of the embodiments are presented in summary below:

The use of a "Patient Clinical Object" (PCO). This term is coined as a semantically rich aggregation of clinical entities that encapsulates information about a given patient. This PCO contains information about the patient and its (a) clinical data, (b) diagnoses, (c) treatments, (d) symptoms and (e) drugs; this information is linked to the healthcare resources/entities. Moreover, this PCO evolves by including more medical information about the patient along the time. Finally, the PCO includes pointers to non-textual data, such as images, audio-clips, ECG/EEG charts, etc. Effectively a PCO is a graph with vertices corresponding to the patient and to clinical information about the patient. The edges between the vertices may be directed from the patient to the clinical information. The PCO provides significant entities encapsulating key mission-critical knowledge about a patient and edges depicting the relationships among the vertices.

An automated vertex filtering component, which (a) relies on domain specific information to compute degree of affinity of vertex, (b) filters vertices according to a pre-defined threshold. It is worth noting each vertex represents a particular feature of the patient as an element of PCO and the direct neighbours of a patient vertex consist of a significant subset of his/her PCO.

The system of the embodiments may include or access a network of computers each responsible for the data processing of a particular type of data (e.g. a computer/server dedicated to the processing of medical literatures such as PUBMED—PUBMED is a service of the US National Library of Medicine (NLM) and provides free access to the NLM database of nursing, veterinary, healthcare, medical and scientific articles, ATC—Anatomical Therapeutic Chemical Classification, ICD9 & ICD10—the ninth and tenth revisions of the International Classification of Diseases), SNOMED—SNOMED CT (clinical terms) is a standardized multilingual vocabulary which is generally applicable across medical and health care areas).

Figure 3:
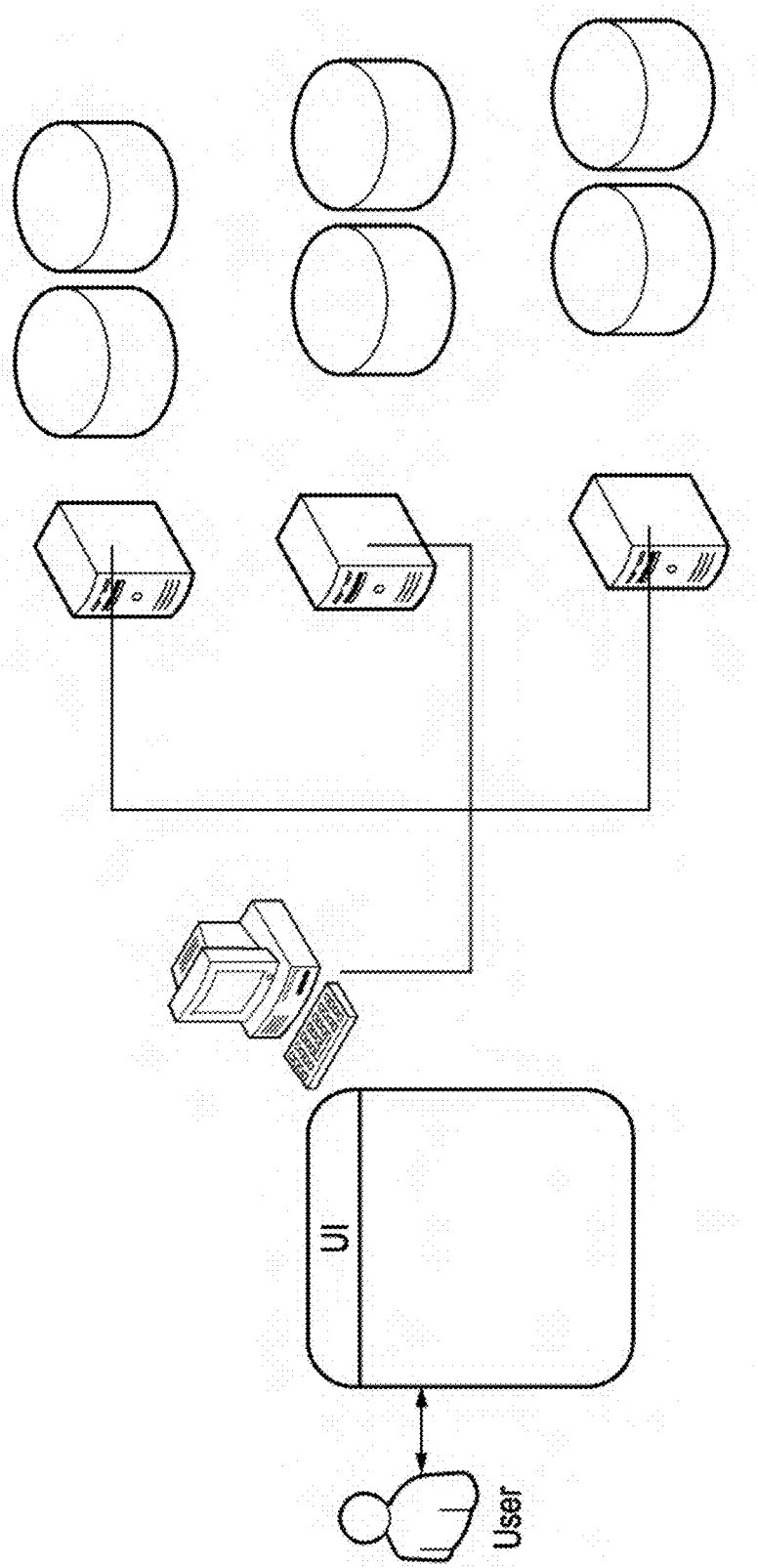
FIG. 3 is a diagram of a suitable hardware configuration for implementation.

Such dedicated computers may be physically separate or provided as a virtual server running on shared physical machines. Such data may be stored locally on the server/computer and queried by the users who access the system through a user UI on a client machine. FIG. 3 illustrates this hardware configuration. Here, the user accesses data via a user interface, UI, and a client computer, which may itself be a server and which communicates (for example over the internet) with various servers accessing or including databases.

Typically, the user selects a patient by identifiable attributes (e.g. names, IDs, etc.), and triggers a similar patient search function supported by client software, as will be explained in more detail later. When the search completes, a list of similar patients may be displayed on the UI, each associated with a numeric similarity value. Further processing may give display of a predicted diagnosis, for example, or predicted treatment.

Figure 4:
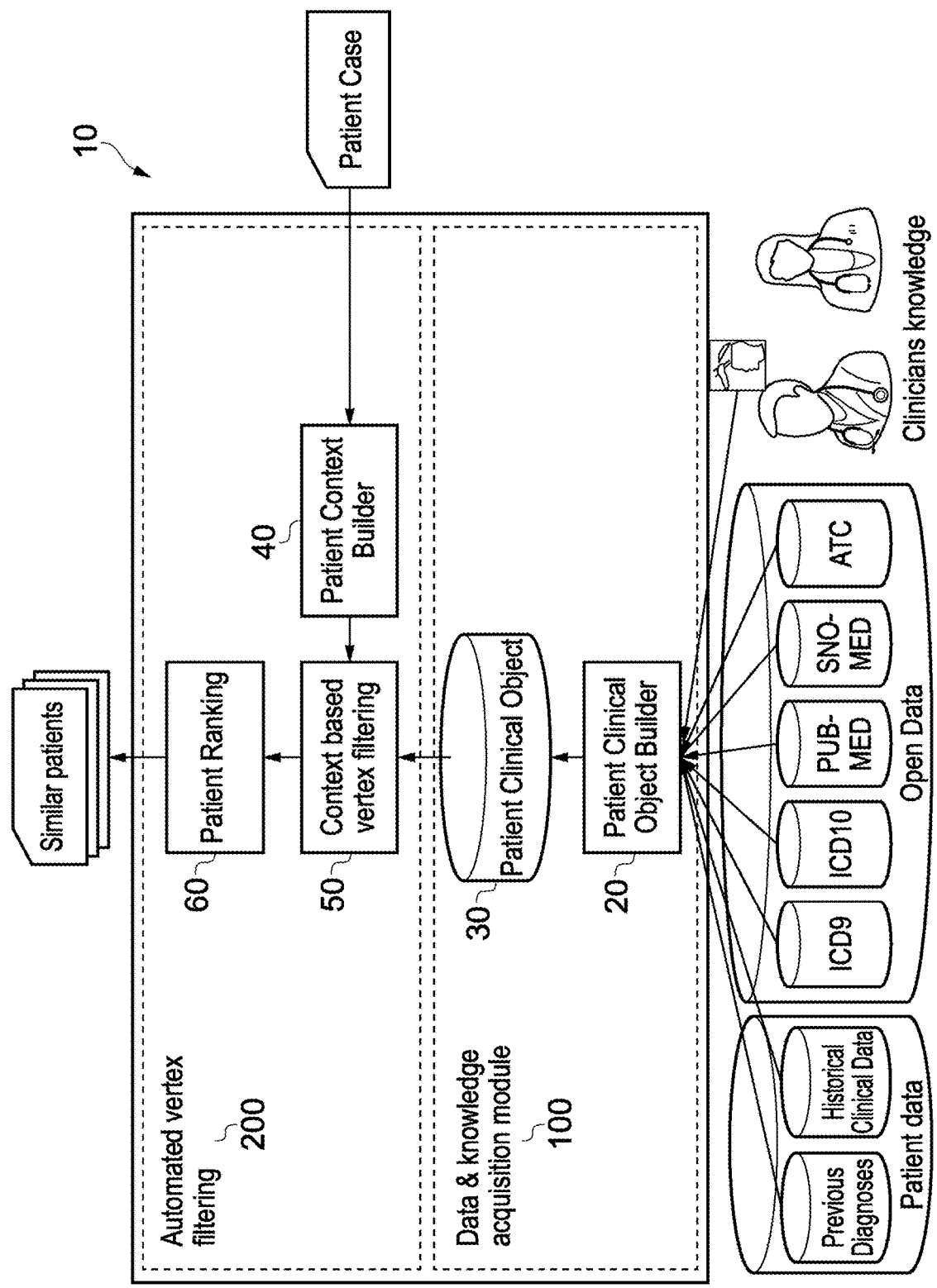
FIG. 4 is a system diagram.

The software running on the above system of FIGS. 1 and 3 includes two main modules described in FIG. 4. FIG. 4 includes a system 10 with data & knowledge acquisition module 100 and automated vertex filtering 200.

100. Data & knowledge acquisition module

This module takes as input the following information

Expert knowledge provided by doctor/clinicians in the form of rules coded in a computer language. The clinicians input the rules as text plain files. Basically, the file consists of several rows, and each row contains 2 diagnoses and the relation between them. For example:

Diagnosis1,relationA,Diagnosis2
Diagnosis3,relationB,Diagnosis4

Examples of rules are incompatible diagnoses, and prevalence of diagnosis 290.0, prevailing over, 290.4
300.0, incompatible with, 309

Where 290.0 corresponds to Senile dementia, uncomplicated, and 290.4 corresponds to Vascular dementia. Also, 300.0 corresponds to Anxiety states, and 309 corresponds to Adjustment reaction.

Previous diagnoses provided by other clinicians as they are recorded in the patient clinical history. These diagnoses will be based on existing international standards such as ICD9 and ICD10.

Data related to the patient's visits to the hospital and the associated points of care, including the frequency, timeframe, and what resources the patient has used.

Biomedical research literature, extracted from literature repositories such as PUBMED, related to diagnoses, diseases, treatments, etc.

Prescription and dispensing of drugs, and their adverse drug reaction, based on European and international standards, such as ATC.

A set of knowledge extracted from available medical standards such as SNOMED.

The expert knowledge need not be essential to make the PCO, but can be used to verify and potentially enrich the knowledge in the PCO, for example by adjusting the diagnoses in the PCO using the expert knowledge, to make sure they are in line with current medical thinking. Additionally or alternatively, any diagnoses in the PCO which are in contradiction with the expert knowledge may be highlighted to the user for manual input and in this way the expert knowledge can act as a cross-check for the quality of the PCOs.

The open data (in the last 3 bullet points above) is used for enrichment of the terms.

The patient builder or patient clinical object builder 20 in this module collects, extracts, integrates, curates and cleans the aforementioned data sources and produces the Patient Clinical Object 30 (or patient's egocentric network or ego-net) for each patient, which contains all the related information about the patient, namely age group, gender, a list of hospital visits grouped by unit, e.g., emergency room, outpatient, inpatient, and day hospital, and a list of previous diagnoses grouped by hospital visits and units.

The PCO may be enriched by equating PCO parts with standard vocabulary from the classifications listed above and hence annotating entities in the patient data as necessary with corresponding concepts/information from the open data. This facilitates later use of the PCO in conjunction with other standard data.

Figure 5:
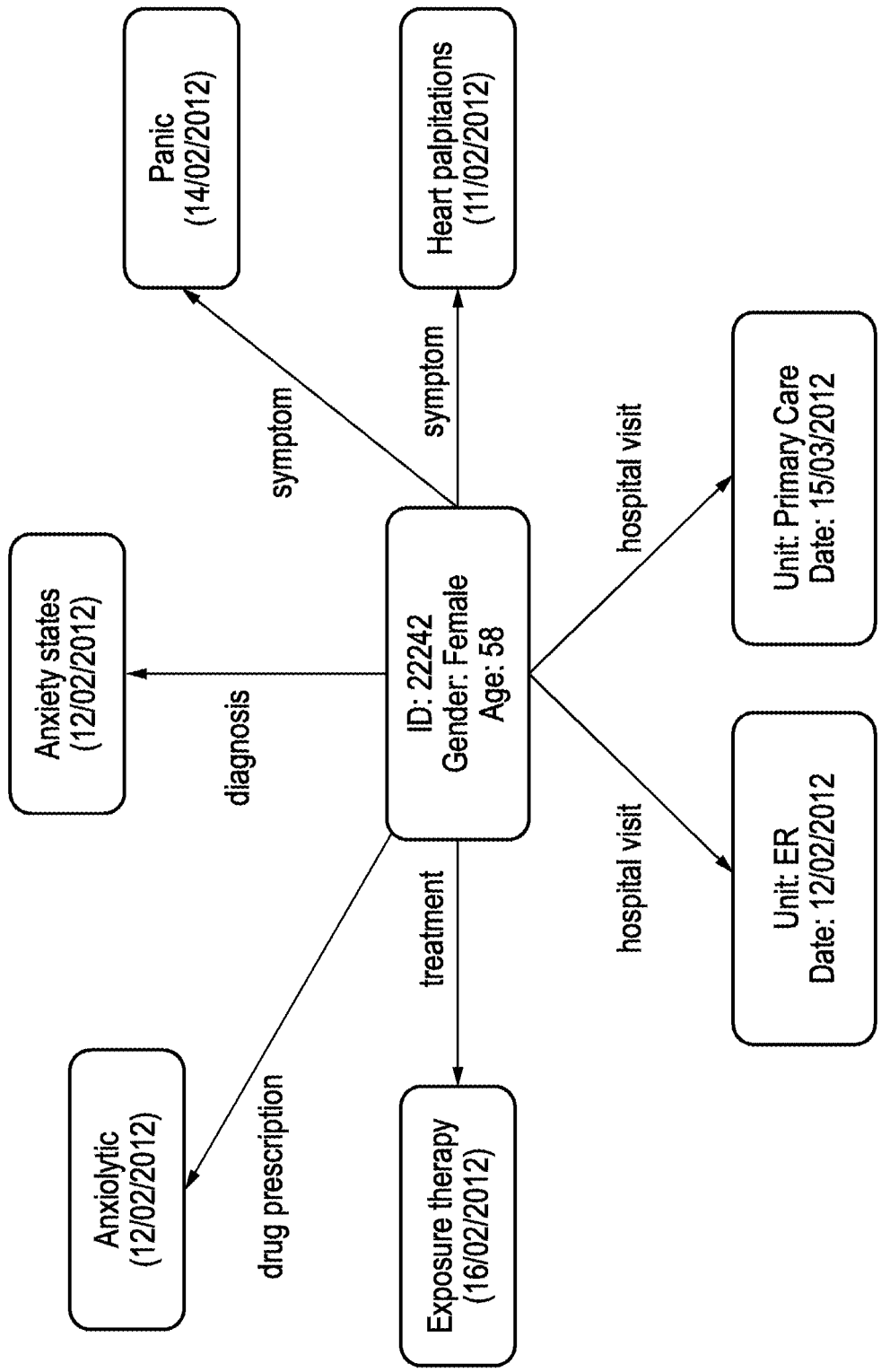
FIG. 5 is an example of a PCO.

A graph format is selected to represent patient data. This is mainly due to the flexibility and versatility of such a modeling paradigm. The graph used in this embodiment is a directed, labeled attribute graph. A graph is a five-tuple $\langle V, E, l_v, l_e, attr \rangle$. Given A as the set of admissible strings—the set of edge and vertex labels l are not necessarily disjoint sets, the labels can be overlapping but edge and vertex should be disjoint. In other words, in cases where one label is used for both vertex and edge, its reference should be clear from the context The five-tuple is defined as:
V is a finite site of vertices,
E a finite site of edge: $e \in E$: $e = \langle u, v \rangle$, $u, v \in V$,
$l_v$ a mapping: $V \times A$
$l_e$ a mapping: $E \times A$
attr a mapping: $V \times A^2$ FIG. 5 illustrates fragments of a patient's ego-net or PCO: a subgraph including the subject patient and all those vertices directly related to the patient (or direct neighboring vertices). Key-value pairs such as "Gender: Female" and "Age: 58" are attributes of the patient vertex (labeled as 22242).

The full patient graph is composed as follows: a vertex is created for each patient. The patient vertex contains attributes, e.g., ID numbers. Symptoms, medications, treatments, and diseases are key entities in the domain of discourse and are also modeled as vertices in the graph. Whether a piece of information is modeled as a vertex with labeled edge connecting it to the patient vertex or modeled as a vertex attribute is based on the following heuristic rules: if the data is of numeric, boolean or other primary data types, it is treated as vertex attribute. Otherwise, it is considered a graph vertex. Moreover, if this piece of information can be further breakdown into finer details, it should be treated as a graph vertex where the further breakdowns become attributes. Also, if the data is considered a specification of a more general concept/category, it will be considered as vertex; otherwise, it will be treated as attributes. For instance, the name of a patient is considered as an attribute while his or her career can be treated as a vertex (or instance in a domain knowledge model).

Effectively, a complete patient egocentric network (also known as PCO) presents a patient profile as a subgraph within the full graph: it is part of the graph representing the domain of discourse. So patient vertices have links to other types of vertices in the graph, such as instances of doctors who treat the patient, and instances of hospitals where the patient is treated. Others vertices include diseases of the relevant domain, treatments, drugs, symptoms, clinical methods, etc.

The PCO of the patient to be diagnosed is also part of the full graph. In general, the full graph should contain both concepts and instances of the domain of discourse. A particular patient is an instance in the full graph. Together with its direct neighbors, it forms a subgraph that can be extracted from the full graph to provide a view of the patient.

In the healthcare domain, certain attributes of patients are considered of higher significance compared to others. Such attributes are selected from a predefined list based on the particular clinical domains within which the patient is inspected. In the above example, gender and age attributes are frequently used to filter a cohort of patients, while names and titles may not present much clinical significance in understanding patient situations. In practice, such attributes are utilized by human experts and/or computer-based systems to filter, rank, or compare patient cases.

Non-Textual Data

Figure 6:
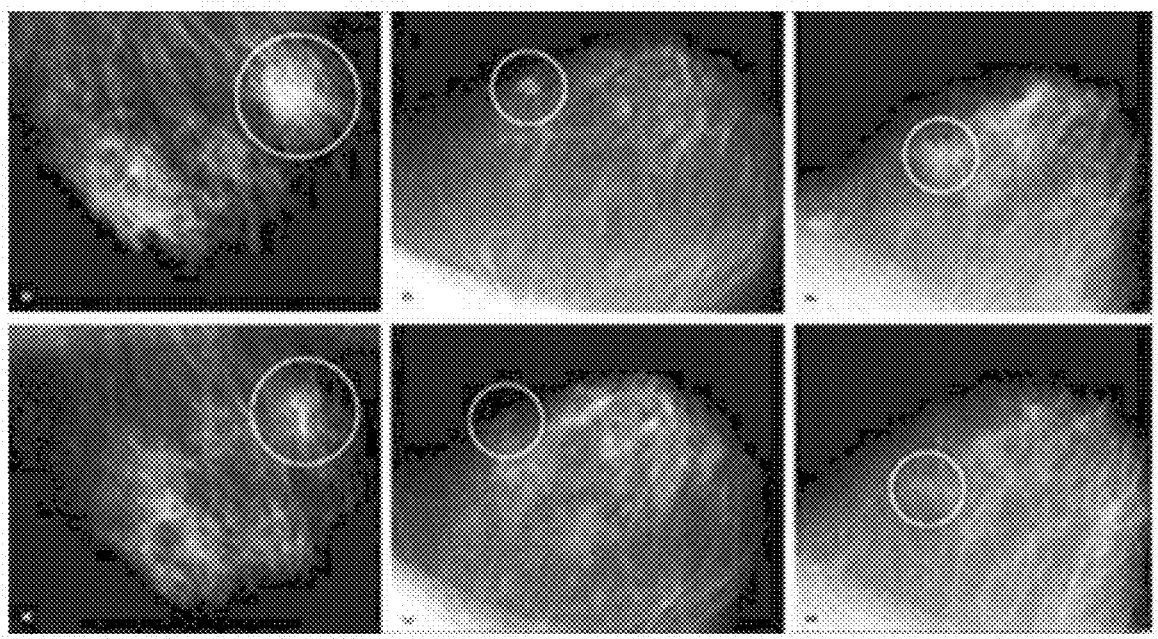
FIG. 6 is an example of non-textual (image) data.

In many clinical situations, non-textual data are used, e.g., images, audio-clips, ECG/EEG charts, MRI stacks, etc. Though it is possible to compare raw non-textual data, such a process is normally very expensive to perform at run time. In the embodiments, textual descriptions are extracted from such data and indexed to improve efficiency. Many existing tools can help in description generation. For instance image analysis tools can be applied to a mammogram to detect and classify abnormalities on the image. In the following, regions are cycled and classified as for instance, "lesion: mass;

shape: irregular; margins: spiculated . . . ". FIG. 6 includes some of these medical images.

Instead of raw image data, such textual description is likely to be the data that clinicians use for initial screening of historical cases.

When constructing the patient network, feature extraction and high level knowledge extraction methods should be applied to such data to generate textual descriptions as part of the data pre-processing step. Outcomes of such a pre-processing step are then stored as vertices in the network graph with pointers leading to the raw data. The raw data, however, are not discarded. Description vertices normally contain pointers to the address where the raw data can be retrieved (either from main memory or disks).

Time Stamping

A key attribute of graph vertices (being patients and other PCOs) is the time stamp of creation. This should reflect the actual creation time in the physical world. For instance, when the MRI image was taken or when a diagnosis was given and a drug was administrated. System create time can also be present for graph data management purposes, but this is not mandatory.

Ego-Centric Patient Network (PCO)

The ego-centric patient network is composed by extracting all the relevant information of a patient and iteratively retrieving all the direct neighbors of patient vertex. In an integrated HIS, patient data are collected from different sources reflecting a wide variety of different aspects of the patient. A patient's ego-net therefore can potentially record all the interaction between an individual and different branches of the healthcare service, being family doctors, pharmacies, out-patient centre, hospital, A&E, day care centers, etc. Ideally, an integrated health information system should provide such a complete picture of involved individuals. In practice, data are expected to be incrementally added to the system through automated data collection/crawling services or manual input. As a result, the patient ego-net can contain a large number of symptom, medication/treatment, and disease vertices. This can put stress on patient similarity computation when high dimensional data need to be compared.

Automated Vertex Filtering

There are potentially a plethora of vertices neighboring a patient vertex. All such neighboring vertices allegedly contribute to patient similarity but at different significance. For instance, for breast cancer cases, the mammography and MRI test results associated with a patient may play a more significant role compared to cognitive examination results. On the other hand, when examining a patient with mental disorder, his/her behavior, family history, genetic testing results, or event facial and voice patterns are more vital while other types of data are considered to be of lower priority. Moreover, among those data that are considered highly relevant, different pieces of data still can contribute to the overall clinical decision making in different significance.

Figure 7:
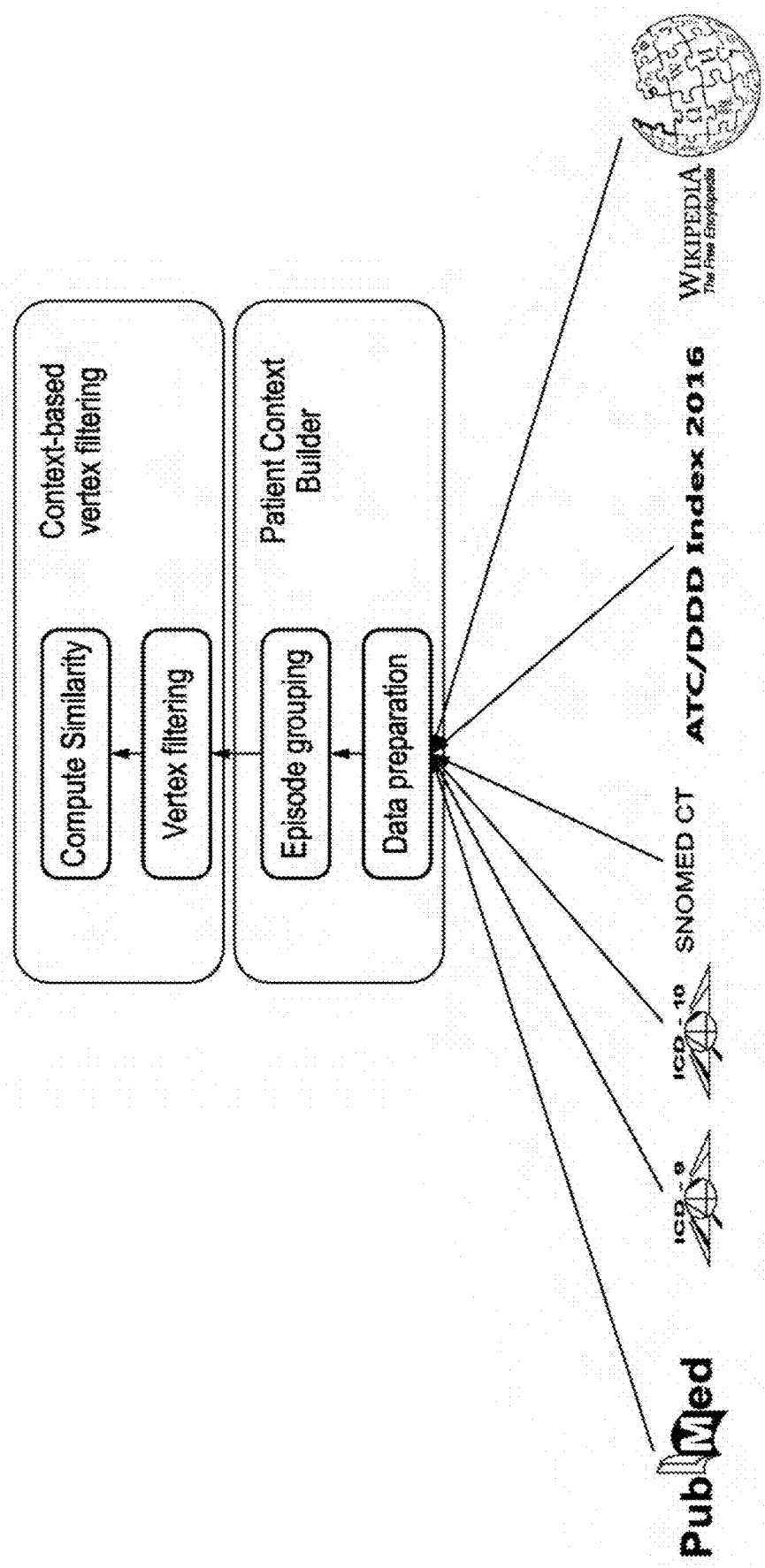
FIG. 7 is a flow diagram of functionality of vertex filtering in embodiments.

FIG. 4 shows the software modules that carry out vertex filtering. These are the patient context builder 40, the context-based vertex filter 50, and the patient ranker 60. Their function is described in FIG. 7, which shows the vertex filtering main tasks and activities.

Such an adaptive vertex filtering approach is conducted as follows:

Data Preparation (Patient Context Builder)

The starting element for data preparation is likely to be based on user interaction. For instance, the user instructs the system to collect data in one or several domains/sub-domains of medicine.

The PCO of the patient to be diagnosed and of other patients is part of formalized domain knowledge. The data preparation however aims at non-formalized data. The data collection process should be automated and only requires limited user interaction for bootstrapping (initial start-up). This interaction, for instance, can be that users choose a domain (e.g. mental health) or several domains and inform the system, which will start data collection around the given domain(s).

For instance, for mental health, the system will first construct a list of core terms by either consulting a define ontology for core concepts in the domain or open data (e.g. Wikipedia) for diseases in this selected domain. When an ontology is used, this ontology is a predefined or an existing one. With this list of core terms, the system can then query web sites such as PUBMED or Wikipedia to retrieve full text description related to such core terms. The collection of all retrieved full text descriptions will form the text corpus for the selected domain 1. Corpus construction: a text corpus is constructed by gathering from public or specific sources, e.g., Wikipedia.
2. Data refinement: this corpus is subject to essential Natural Language Processing (NLP) processing steps to perform stop word removal, plural folding, stemming, etc. Many open source libraries can be applied for this task.
3. Feature vector extraction: refined data is then processed to extract features. Many different technologies can be applied here, e.g. Singular Value Decomposition (SVD) or Artificial Neural Network (ANN).

The outcome of this preparation is a domain specific list of n-dimensional vectors, each embedding a term that plays a vital role in defining this domain. An example is of the following form:

Parkinson (0.755,0.682,0.723, . . . )

The semantics of vector elements varies depending on the extraction technologies used: if a predefined set of features is used, the numeric value can signify significance of the corresponding feature present in the context of the target word (in the above example "Parkinson"). If an automatic featuring method is used (e.g. a convolutional neural network model), the features may not be explicitly defined. In this case, the numeric values still indicate the significance of unnamed features in the context of the given word.

Episode Grouping (Patient Context Builder 40)

Episode grouping is on a per-patient basis. The full graph may contain instances of clinical methods of several disease of a patient. Basically, as a complete domain knowledge graph, it should provide full (visible) history of a patient among other things. For instance, a patient's ego-net may contain his/her information regarding an episode of chest infection and an episode of depression. These two episodes may occur in consecutive periods. It is necessary to differentiate them when computing contexts. The episode grouper will help the system to group related instances together among all the other instances from a patient's ego-net.

The vertices are grouped based on time-based episodes. Here, standard, off-the-shelf episode groups can be used. Otherwise, a method as proposed in UK Patent Application number GB1615986.5 filed on 20 Sep. 2016 can be used. This application is incorporated herein by reference.

Since all vertices are time-stamped, one implementation could simply be based on time gap between the creations of different vertices. For instance, in practice, many insurers take a threshold of 6 weeks as the minimum length of time elapse between two consecutive visits to any clinical establishments that divides these visits to separate disease episodes. All the vertices whose time gap is smaller than the threshold are grouped as belonging to one single episode.

Vertex Filtering (Context-Based Vertex Filtering 50)

Within each episode, vertices are filtered and/or ranked based on their domain affiliation, e.g., mental disorders or breast cancers) with the domain as defined above. These vertices are only those which refer to symptoms, medications, treatments and diseases, rather than patient ID vertices. As it works on an ego-centric network which has the patient as the central vertex, the filtering will be only based on other types of vertices that can help to understand the context of a patient (which is explicitly identified by the ID.

1. Using the domain specific vectors, a degree of affinity of a vertex label with the domain is computed. This maps the vertex label to the language model obtained above and computes the aggregated similarity between the full vertex label and the core set of terms in the language model. The core set can be composed by either manually selecting a set of representative words/terms or the top-n most frequent words/terms in the domain.
2. Filtering vertices
    a. If a threshold is defined, those vertices with lower affinity than the threshold are filtered out.
    b. Otherwise, the top n (again predefined by the users) of the vertices are selected.

Compute Similarity (Context-Based Vertex Filter 50)

The similarity is computed based on the context of domain and episode.

Once filtered, the remaining vertices with respect to a single patient can then be used to compute similarity to the patient to be diagnosed in the context of a given domain of discourse (e.g. mental disorders or breast cancers). This on a per-patient and per-episode basis, for each PCO in the full graph.

The similarity computation can be simply performed as follows:

1. As highlighted in FIG. 5, all vertices belong to a particular category (as instances of concepts). Labels of those belonging to the same category can then be concatenated into a string.
2. Similarity of vertices of the same category can be computed using for instance string similarity algorithms as $\sigma_{c_i}(a,b)=\text{jaro\_winkler\_distance}(a,b)$.
3. Affinity values are applied to adjust such similarity: $\text{sim}_{c_s}(a,b)=\alpha \cdot \sigma_{c_i}(a,b)$ Affinity here refers to the affinity of a word with respect to the domain of discourse.
4. Overall similarity is then computed as: $\text{sim}=\text{agg}(\Sigma_i \text{sim}_{c_i}(a,b))$, where the aggregation function can be implemented by many different approaches. For instance, a simple approach can be weighted average.

Ranking (Patient Ranker 60)

The ranker simply takes the similarity from the context-based vertex filter and produces a ranked list, with a possibility for manual input by the user to adjust the rankings and/or members of the list.

It should be noted that the full graph is for domain modeling and formalization. When computing patient similarity, the processes are based on each individual PCO.

Other Technological Fields

These embodiments primarily target the healthcare domain. The underlying technologies, however, can be applied to other domains. For instance, they can be used in legal and legislation areas, where searching and referencing precedent is necessary. When applied to another domain, new domain knowledge model need to be constructed with suitable data.

In a nutshell, finding similar patients to a given one will help to provide the right diagnosis and/or treatments and even prognosis, and help with the prediction of the evolution of that patient.

Embodiments may provide:

1. A method to dynamically filter features that are of higher importance to the subject domain, as and when a new diagnosis is required for a patient;
2. A method that based on the filtering also automatically adjusts case similarity to reflect the focus of a domain of discourse;
3. A component that ingest data from different sources to compose a patient centric graph;
4. A system, implementing the above methods, that facilitates automatic retrieval and ranking of historical cases to support decision making.

BRIEF DESCRIPTION OF TECHNICAL TERMS USED

HIS: hospital information system.

EHR: Electronic health records.

Prognosis: a forecasting of the probable course and outcome of a disease, especially of the chances of recovery.

Diagnosis: the process of determining by examination the nature and circumstance of a disease or condition from its signs and symptoms.

Medical treatment: the management and care of a patient, including for example in the mental health area, nursing, psychological intervention and specialist mental health rehabilitation. This term may also include "alternative" medical treatments and medication which may be prescribed, if so wished, for example, homeopathic/hypnosis/acupuncture treatment.

Drugs: medications that treat or prevent or alleviate the symptoms of a disease or condition.

Although a few embodiments have been shown and described, it would be appreciated by those skilled in the art that changes may be made in these embodiments without departing from the principles and spirit thereof, the scope of which is defined in the claims and their equivalents.

What is claimed is:

1. A computer, comprising:
    a processor to couple to a memory, the memory storing instructions for execution by the processor, the processor configured by the instructions to provide an automated patient builder and an automated patient vertex filter;
    wherein:
        the automated patient builder is to,
            input, for a population of patients, electronic patient data of a patient, among the patients, the electronic patient data including historical clinical data and open data, the historical data including raw non-textual data,
            create patient clinical objects (PCOs) representing the population of patients, respectively, based on the electronic patient data, and
            enrich the electronic patient data of each patient of the patients, respectively, based on the open data, the PCOs being created by pre-processing the electronic patient data for automated filtering, the pre-processing including extracting, using an automated extraction technology, textual information from the raw non-textual data of the electronic patient data to store each PCO of the PCOs in the memory in form of pieces of at least the extracted textual information modeled as vertices with edges among the vertices forming a graph, resulting in the extracted textual information being a labeled vertex of a corresponding PCO among the PCOs,
    each vertex of the vertices electronically encapsulating knowledge about the patient in form of the textual data of the electronic patient data, and including a pointer leading to an address in the memory to link each vertex to where the raw non-textual data represented by the vertex is retrievable from the memory,
    the vertices to form the graph centered on a patient ID vertex, among the vertices, indicating a patient ID, with the edges representing relationships among the vertices by linking the patient ID vertex to the vertices labeled to represent the historical clinical data of the electronic patient data belonging to a category according to the enriched electronic patient data, respectively, and
    each PCO of the PCOs representing the patient as a subgraph, wherein vertices corresponding to a plurality of subgraphs respectively corresponding to each PCO of the PCOs together compose vertices corresponding to a full patient graph of the PCOs representing the population of patients;
the patient vertex filter is to perform the automated filtering on the vertices corresponding to the full patient graph to indicate at least one diagnosis corresponding to a target PCO of a target patient, from among the full patient graph, by implementing:
    a patient context builder to input, for the target PCO of the target patient, a specification of a medical domain according to a context and the open data used to enrich the patient data of the target patient, to a singular value decomposition (SVD) technology and/or artificial neural network (ANN) to extract feature vectors to obtain a context-based domain corpus based on the context and the open data,
    a context-based vertex filter to,
        filter based on ranking the vertices in the full patient graph based on vertex domain affiliation with respect to the context-based domain corpus for the target PCO, to retain vertices, in each PCO of the other PCOs in the full patient graph, with high context-based domain affiliation to the target PCO, and
        compute similarity values between the target PCO and the other PCOs on basis of the retained vertices, and
    a patient ranker to rank the PCOs in the full patient graph according to the computed similarity values between the target PCO and the other PCOs, resulting in a contextualized list of similar PCOs; and
the processor is further configured by the instructions to indicate the at least one diagnosis corresponding to the target PCO, based on the ranked computed similarity values between the target PCO and the other PCOs within the full patient graph in the contextualized list of similar PCOs.

2. A computer apparatus according to claim 1, further comprising:
an episode grouper within the patient vertex filter which groups vertices of each PCO of the PCOs into time-based episodes.

3. A computer apparatus according to claim 2, wherein:
the episode grouper groups the vertices using a time stamp of data creation.

4. A computer apparatus according to claim 2, wherein:
the context-based vertex filter and the patient ranker process each episode of each PCO of the PCOs separately.

5. A computer apparatus according to claim 1, wherein:
the context-based vertex filter groups the vertices in each PCO of the PCOs of a same category together and calculates a similarity of the grouped vertices with vertices of the same category in the target PCO, using vertex labels.

6. A computer apparatus according to claim 5, wherein:
the context-based vertex filter adjusts a calculated similarity of the grouped vertices with vertices of the same category in the target PCO, by applying an affinity value indicative of affinity of the grouped vertices with the same category with the context-based domain corpus for the target PCO.

7. A computer apparatus according to claim 1, wherein:
the patient builder accepts input from an automated data crawler, to update a PCO from among the PCOs incrementally.

8. A computer apparatus according to claim 1, wherein:
the patient builder additionally accepts expert knowledge in form of clinician's rules, to verify a diagnoses in the PCO.

9. A computer apparatus according to claim 1, wherein:
the patient context builder provides the context-based domain corpus in form of a domain-specific list of vectors, each list embedding a term defining a domain, with values of the vector indicating a significance of a term.

10. A computer apparatus according to claim 1, wherein:
the open data is input from more than one source.

11. A computer apparatus according to claim 1, wherein:
the context-based vertex filter retains vertices with high domain affiliation in each PCO by one of:
filtering out vertices with a domain affiliation below a threshold; and
ranking the vertices in order of domain affiliation and selecting a predefined number of vertices starting from a highest domain affiliation.

12. A computer implemented method, comprising:
by a processor coupled to a memory and configured to automatically,
    input, for a population of patients, electronic patient data of a patient, among the patients, the electronic patient data including historical clinical data and open data, the historical data including raw non-textual data,
    create patient clinical objects (PCOs) representing the population of patients, respectively, based on the electronic patient data, and
    enrich the electronic patient data of each patient of the patients, respectively, based on the open data,
        the PCOs being created by pre-processing the electronic patient data for automated filtering, the pre-processing including extracting, using an automated extraction technology, textual information from the raw non-textual data of the electronic patient data to store each PCO of the PCOs in the memory in form of pieces of at least the extracted textual information modeled as vertices with edges among the vertices forming a graph, resulting in the extracted textual information being a labeled vertex of a corresponding PCO among the PCOs, each vertex of the vertices electronically encapsulating knowledge about the patient in form of the textual data of the electronic patient data, and including a pointer leading to an address in the memory to link each vertex to where the raw non-textual data represented by the vertex is retrievable from the memory, the vertices to form the graph centered on a patient ID vertex, among the vertices, indicating a patient ID, with edges representing relationships among the vertices by linking the patient ID vertex to the vertices labeled to represent the historical clinical data of the electronic patient data belonging to a category according to the enriched electronic patient data, respectively, and each PCO of the PCOs representing the patient as a subgraph, wherein vertices corresponding to a plurality of subgraphs respectively corresponding to each PCO of the PCOs together compose vertices corresponding to a full patient graph of the PCOs representing the population of patients;

filter the vertices corresponding to the full patient graph to indicate at least one diagnosis corresponding to a target PCO of a target patient, from among the full patient graph, by:

inputting, for the target PCO of the target patient, a specification of a medical domain according to a context and the open data used to enrich the patient data of the target patient, to a singular value decomposition (SVD) technology and/or artificial neural network (ANN) to extract feature vectors to obtain a context-based domain corpus based on the context and the open data, filtering based on ranking the vertices in the full patient graph based on domain affiliation with respect to the context-based domain corpus for the target PCO and retaining vertices, in each PCO of the other PCOs in the full patient graph, with high context-based domain affiliation to the target PCO, computing similarity values between the target PCO and the other PCOs on a basis of the retained vertices, and ranking the PCOs in the full patient graph according to the computed similarity values between the target PCO and the other PCOs, resulting in a contextualized list of similar PCOs; and indicating the at least one diagnosis corresponding to the target PCO, based on the ranked computed similarity values between the target PCO and the other PCOs within the full patient graph in the contextualized list of similar PCOs.

13. A non-transitory computer-readable medium storing a computer program which when executed on a computer carries out a method comprising:

automatically inputting, for a population of patients, electronic patient data of a patient, among the patients, the electronic patient data including historical clinical data and open data, the historical data including raw non-textual data, creating patient clinical objects (PCOs) representing the population of patients, respectively, based on the electronic patient data, and enrich the electronic patient data of each patient of the patients, respectively, based on the open data, the PCOs being created by pre-processing the electronic patient data for automated filtering, the pre-processing including extracting, using an automated extraction technology, textual information from the raw non-textual data of the electronic patient data to store each PCO of the PCOs in the memory in form of pieces of at least the extracted textual information modeled as vertices with edges among the vertices forming a graph, resulting in the extracted textual information being a labeled vertex of a corresponding PCO among the PCOs, each vertex of the vertices electronically encapsulating knowledge about the patient in form of the textual data of the electronic patient data, and including a pointer leading to an address in the memory to link each vertex to where the raw non-textual data represented by the vertex is retrievable from the memory, the vertices to form the graph centered on a patient ID vertex, among the vertices, indicating a patient ID, with edges representing relationships among the vertices by linking the patient ID vertex to the vertices labeled to represent the historical clinical data of the electronic patient data belonging to a category according to the enriched electronic patient data, respectively, and each PCO of the PCOs representing the patient as a subgraph, wherein vertices corresponding to a plurality of subgraphs respectively corresponding to each PCO of the PCOs together compose vertices corresponding to a full patient graph of the PCOs representing the population of patients;

filtering the vertices corresponding to the full patient graph to indicate at least one diagnose corresponding to a target PCO of a target patient, from among the full patient graph, by:

inputting, for the target PCO of the target patient, a specification of a medical domain according to a context and the open data used to enrich the patient data of the target patient, to a singular value decomposition (SVD) technology and/or artificial neural network (ANN) to extract feature vectors to obtain a context-based domain corpus based on the context and the open data;

filtering based on ranking the vertices in the full patient graph based on domain affiliation with respect to the context-based domain corpus for the target PCO and retaining vertices, in each PCO of the other PCOs in the full patient graph, with high context-based domain affiliation to the target PCO, computing similarity values between the target PCO and the other PCOs on basis of the retained vertices, and ranking the PCOs in the full patient graph according to the computed similarity values between the target PCO and the other PCOs, resulting in a contextualized list of similar PCOs; and indicating the at least one diagnosis corresponding to the target PCO, based on the ranked computed similarity values between the target PCO and the other PCOs within the full patient graph in the contextualized list of similar PCOs.

* * * * *